United States Patent [19]
Shirasaki

[11] Patent Number: 5,094,245
[45] Date of Patent: Mar. 10, 1992

[54] ELECTRONIC BLOOD PRESSURE METER

[75] Inventor: Osamu Shirasaki, Amagasaki, Japan

[73] Assignee: Omron Corporation, Kyoto, Japan

[21] Appl. No.: 511,961

[22] Filed: Jul. 25, 1990

[30] Foreign Application Priority Data

Oct. 17, 1988 [JP] Japan .................................. 63-260957
Oct. 20, 1988 [JP] Japan .................................. 62-264976
Oct. 21, 1988 [JP] Japan .................................. 63-266694
Oct. 24, 1988 [JP] Japan .................................. 63-267642

[51] Int. Cl.$^5$ ............................................. A61B 5/02
[52] U.S. Cl. ..................................... 128/680; 128/683
[58] Field of Search ................. 128/672, 677, 680–686

[56] References Cited

U.S. PATENT DOCUMENTS

| | | | |
|---|---|---|---|
| 4,664,126 | 5/1987 | Link .................................... | 128/680 |
| 4,712,563 | 12/1987 | Link .................................... | 128/681 |
| 4,754,761 | 7/1988 | Ramsey, III et al. ............... | 128/653 |
| 4,830,019 | 5/1989 | Shirasaki et al. ................... | 128/680 |
| 4,850,368 | 7/1989 | Myawaki ............................. | 128/680 |

Primary Examiner—Ruth S. Smith
Assistant Examiner—Robert L. Nasser, Jr.
Attorney, Agent, or Firm—Fish & Richardson

[57] ABSTRACT

An electronic blood pressure meter in which average pulse wave ratio values are computed from pulse wave data as a ratio of a difference between an average pulse wave level and a minimum pulse wave level to a difference between a maximum pulse wave level and the minimum pulse wave level, and the average pulse wave ratio values are used for evaluating a relationship between said cuff pressure and said pulse wave data. By detecting an interval of a relatively sharp and monotonical increase in the average pulse wave ratio as the cuff pressure is gradually decreased, a systolic blood pressure value and a diastolic blood pressure value are determined as the cuff pressures at the beginning and end of this interval, respectively. As these critical points can be detected with relatively little ambiguity and are not much affected by individual differences, an accurate and reliable blood pressure measurement is made possible. Also, by making use of the average pulse wave ratio, insufficiency in the initial pressurization of the cuff can be detected at a very early stage of blood pressure measurement.

7 Claims, 12 Drawing Sheets

FIG.1

CUFF PRESSURE ≧ SYSTOLIC PRESSURE
FIG.2(a)

CUFF PRESSURE ≑ AVERAGE PRESSURE
FIG.2(b)

CUFF PRESSURE ≦ DIASTOLIC PRESSURE
FIG.2(c)

THRESHOLD LEVEL

ELECTRONIC BLOOD PRESSURE METER

This application is a continuation of U.S. application Ser. No. 07/422,552, filed Oct. 17, 1989, now abandoned.

TECHNICAL FIELD

The present invention relates to an electronic blood pressure meter using a pressurized cuff which is applied to a living body such as a human arm, and in particular to such an electronic blood pressure meter based on an oscillometric process.

BACKGROUND OF THE INVENTION

When a cuff wrapped around a human body part is pressurized to a certain level with a pump and is then gradually depressurized, the internal pressure of the cuff cyclically changes in synchronism with his pulse. This cyclic change in the internal pressure of the cuff is called as pulse wave, and the oscillometric processes generally refer to a number of different processes for determining blood pressure values according to analysis of the wave form of the pulse wave.

Figure 7:
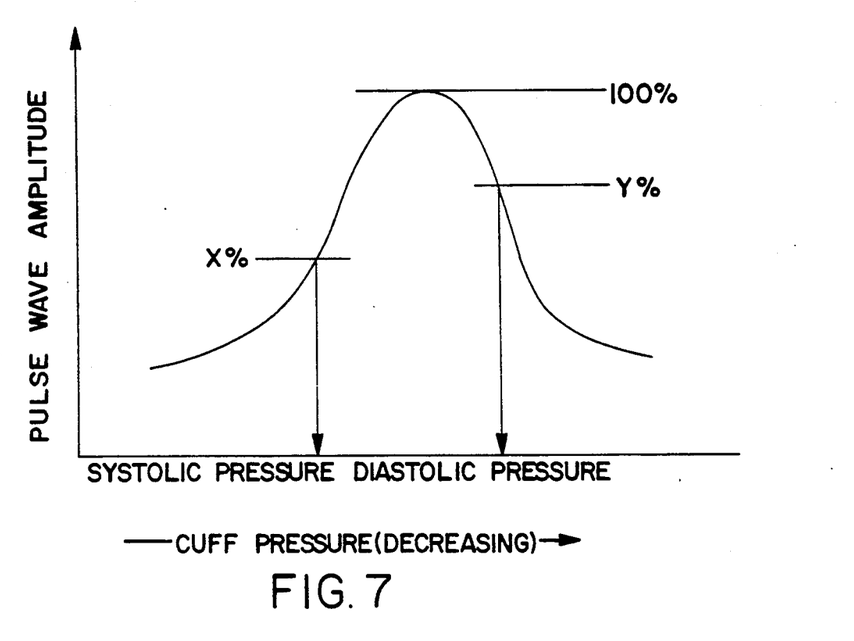
FIGS. 7 and 8 are graphs illustrating the principles of measurement of blood pressures based on other oscillometric processes.

Specifically, when the cuff pressure is increased beyond an expected systolic pressure level and is then gradually decreased, the amplitude of the pulse wave is initially small and gradually increases as the cuff pressure declines. As the cuff pressure reaches near an average blood pressure level, the amplitude of the pulse wave attains a maximum level, and then decreases as the cuff pressure declines further. According one of the oscillometric processes, a systolic pressure and a diastolic pressure are given as the cuff pressures at which the amplitude of the pulse wave becomes equal to certain fractions (X % and Y %) of the maximum amplitude of the pulse wave (refer to FIG. 7). According to another oscillometric process, a systolic pressure and a diastolic pressure are determined as the cuff pressures at which the increase rate of the amplitude of the pulse wave sharply increases and sharply decreases (refer to FIG. 8).

However, the behavior of the amplitude of pulse wave can vary a great deal depending on each individual. In the case of one of the aforementioned oscillometric processes, the true systolic pressure and the true diastolic pressure may not be prescribed fractions of the maximum amplitude of pulse wave. In the case of the other oscillometric process, the points of sharp changes in the change rate of the amplitude of the pulse wave are in many cases unclear. For these reasons, significant measurement errors have been encountered in many cases.

In such oscillometric processes for electronically measuring blood pressure values, the cuff must be pressurized at least beyond a conceivable systolic blood pressure value. When pressurization is not sufficient, an accurate measurement is impossible. Because such insufficiency of pressurization is not discovered until the process of measuring blood pressure has progressed a certain extent, the cuff must be repressurized upon discovery of such an insufficiency and the time required for blood pressure measurement is inevitably prolonged to a considerable extent. Conversely, if the cuff is pressurized excessively, not only the time required for blood pressure measurement will increase because an earlier part of gradual depressurization merely wastes time but also the discomfort of the person wearing the cuff is unduly prolonged.

BRIEF SUMMARY OF THE INVENTION

In view of such technical tasks, a primary object of the present invention is to provide an electronic blood pressure meter which can measure blood pressure values with minimum time and offers a high accuracy at the same time.

A second object of the present invention is to provide an electronic blood pressure meter which is relatively free from error arising from individual differences.

A third object of the present invention is to provide an electronic blood pressure meter which is free from excessive pressurization of the cuff.

A fourth object of the present invention is to provide an electronic blood pressure meter which can quickly readjust itself by quickly detecting any insufficiency of initial pressurization.

These and other objects of the present invention can be accomplished by providing an electronic blood pressure meter, comprising: a cuff for applying a pressure to a living body whose blood pressure is to be measured; pressurization means for initially pressurizing the cuff and then gradually depressurizing it; pressure detecting means for detecting pressure in the cuff as a pulse wave as the cuff is gradually depressurized; pulse wave extracting means for extracting pulse wave data from the a pressure signal obtained by the pressure detecting means; blood pressure computing means for computing a systolic blood pressure value and a diastolic blood pressure value according to the pulse wave data obtained by the pulse wave extracting means; and average pulse wave ratio computing means for computing an average pulse wave ratio as a ratio of a difference between an average pulse wave level and a minimum pulse wave level to a difference between a maximum pulse wave level and the minimum pulse wave level; the average pulse wave ratio being used by the blood pressure computing means for evaluating a relationship between the cuff pressure and the pulse wave data.

As the average pulse wave ratio reflects in clear and pronounced fashion the changes in the pulse wave data, an accurate blood pressure measurement can be made possible through the use of the average pulse wave ratio. Also, by making use of the average pulse wave ratio, insufficiency in the initial pressurization of the cuff can be detected at a very early stage of blood pressure measurement and, therefore, the discomfort to the wearer of the cuff may be minimized.

The average pulse wave ratio may be related to blood pressure values by detecting a maximum value and a minimum value of the average pulse wave ratio as the cuff pressure is gradually decreased, and determining the cuff pressures at those critical points as a systolic blood pressure value and a diastolic blood pressure value, respectively.

Alternatively, a same goal may be achieved by detecting a start and an end of an interval of a relatively sharp and monotonical increase in the average pulse wave ratio as the cuff pressure is gradually decreased, and determining the cuff pressures at those critical points as a systolic blood pressure value and a diastolic blood pressure value, respectively. According to a particularly preferred embodiment of the present invention, the interval of a relatively sharp and monotonical increase is detected by evaluating the magnitudes of second order differentials of the average pulse wave ratio.

Since the required initial pressurization level of the cuff varies considerably from one individual to another, it is preferred than the initial pressurization should not be set at a very high level in order to prevent any unduly prolonged discomfort to subjects who do not require such a high initial pressurization level, and that, should the initial pressurization level be too low for a particular individual, this insufficiency should be detected at as early an stage as possible so that the repressurization of the cuff may be accomplished in a minimum time. To achieve this goal, insufficiency of initial pressurization of the cuff may be detected when an average pulse wave ratio value or an average value of a certain number of average pulse wave ratio values obtained at an early stage of pressurization of the cuff is larger than a certain threshold level and/or a change rate of the average pulse wave ratio is larger than another threshold level.

BRIEF DESCRIPTION OF THE DRAWINGS

Now the present invention is described in the following with reference to the appended drawings, in which.

DETAILED DESCRIPTION OF THE PREFERRED EMBODIMENTS

Figure 1:
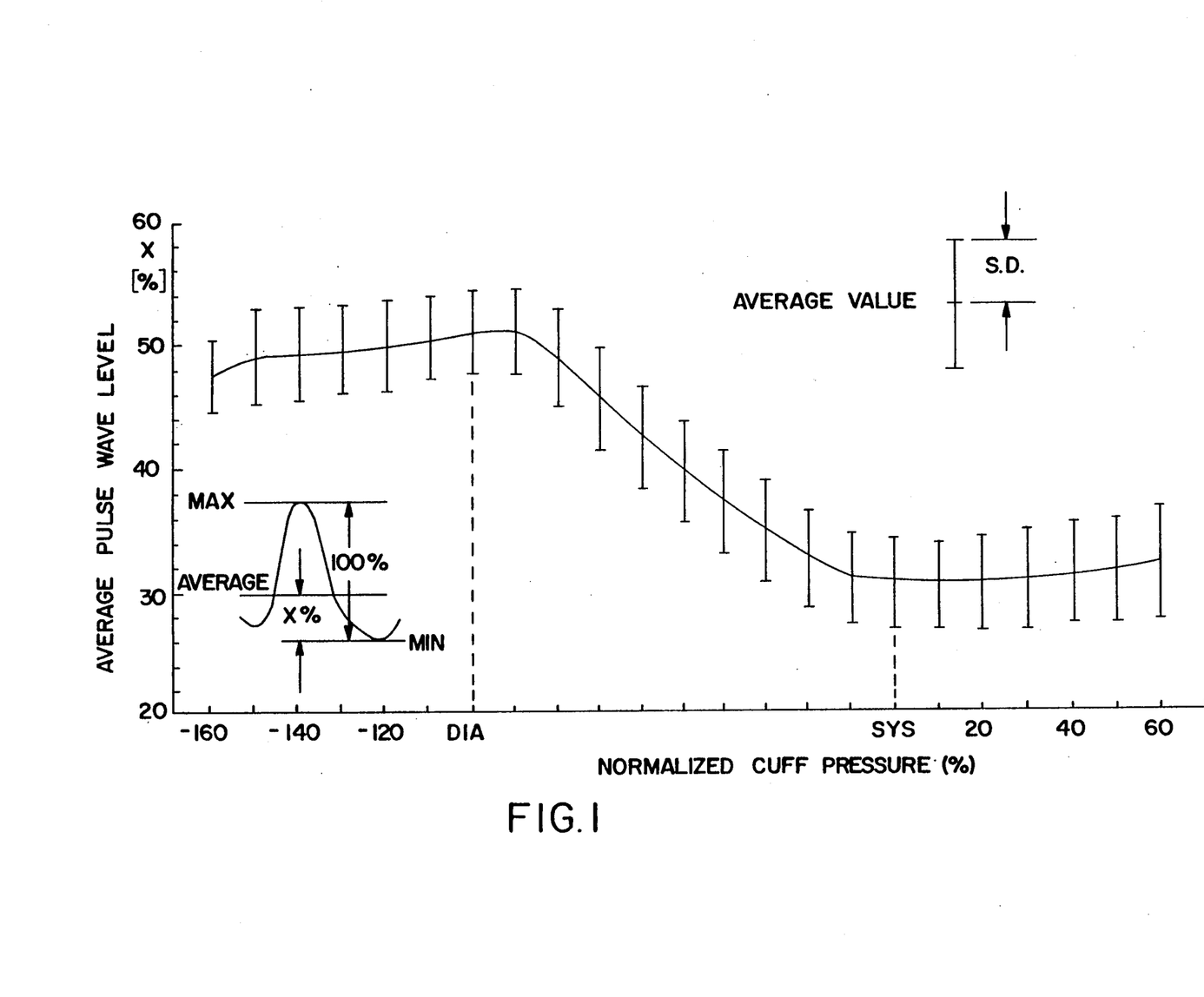
FIG. 1 is a graph showing the relationship between the cuff inner pressure and the average pulse wave level to explain the concept of average pulse wave ratio.

First of all, the properties of average pulse wave ratio are described in the following with reference to FIG. 1 showing the changes in the average pulse wave ratio R as the cuff inner pressure declines. Average pulse wave ratio is given as the ratio of the average level of pulse wave obtained by integration to the peak-to-peak amplitude of the pulse wave, or average pulse wave ratio $R =$ $$\frac{\text{(average value)} - \text{(minimum value)}}{\text{(maximum value)} - \text{(minimum value)}}$$

This graph is made by plotting data obtained from 260 individuals by the conventional stethoscopic measurement process and normalized by a systolic blood pressure SYS and a diastolic blood pressure DIA. The horizontal axis represents the cuff inner pressure which is normalized by setting SYS-DIA as 100% and placing SYS at the datum. From this graph, it can be seen that the pulse wave average ratio R slightly decreases as the cuff inner pressure declines in the region of the cuff inner pressure higher than a systolic blood pressure level SYS but starts sharply increasing when the cuff inner pressure falls below the systolic blood pressure level SYS. The average pulse wave ratio continues to monotonically increase until the inner cuff pressure reaches a diastolic blood pressure level DIA at which the average pulse wave ratio R is approximately 50% of the amplitude of the pulse wave. Thereafter, the average pulse wave ratio R gradually and slightly declines as the cuff pressure further declines.

Figure 2A:
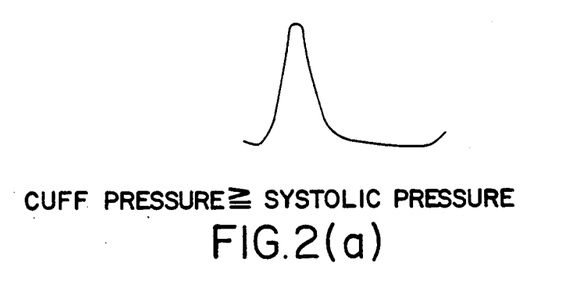
FIGS. 2(a) through 2(b) are wave form diagrams showing the differences in the pulse wave forms depending on the magnitude of the cuff inner pressure.
Figure 2B:
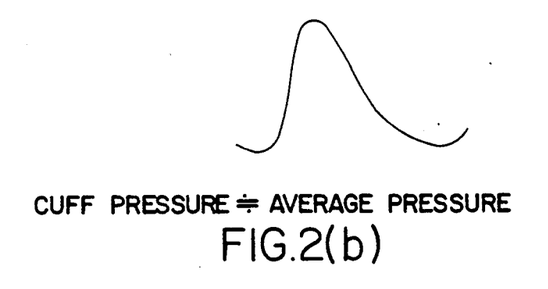
Figure 2C:
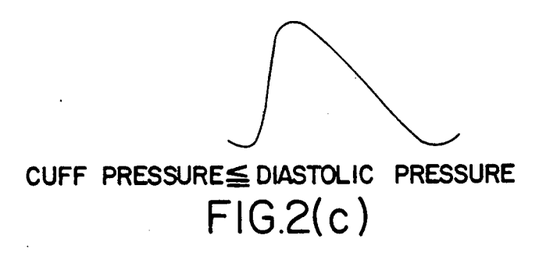

Such changes in the average pulse wave ratio R is based on the changes in the wave form of the pulse wave as illustrated in FIGS. 2(a) through 2(c), and such changes in the wave form of the pulse wave is not only relatively free from individual differences but also easily and clearly detectable. Hence, a highly reproducible blood pressure measurement is possible by using average pulse wave ratio. For instance, a pulse wave component is extracted during the process of depressurizing an arm cuff, a maximum level, a minimum level and an average level are computed from this pulse wave component, critical points in the changes of the average pulse wave ratio are extracted, and a systolic blood pressure and a diastolic blood pressure are computed from the thus extracted critical points.

Although the measurement was assumed to take place during the process of gradual depressurization of a cuff, it should be understood that the same concept may be applied equally during the process of gradual pressurization of a cuff.

Figure 3:
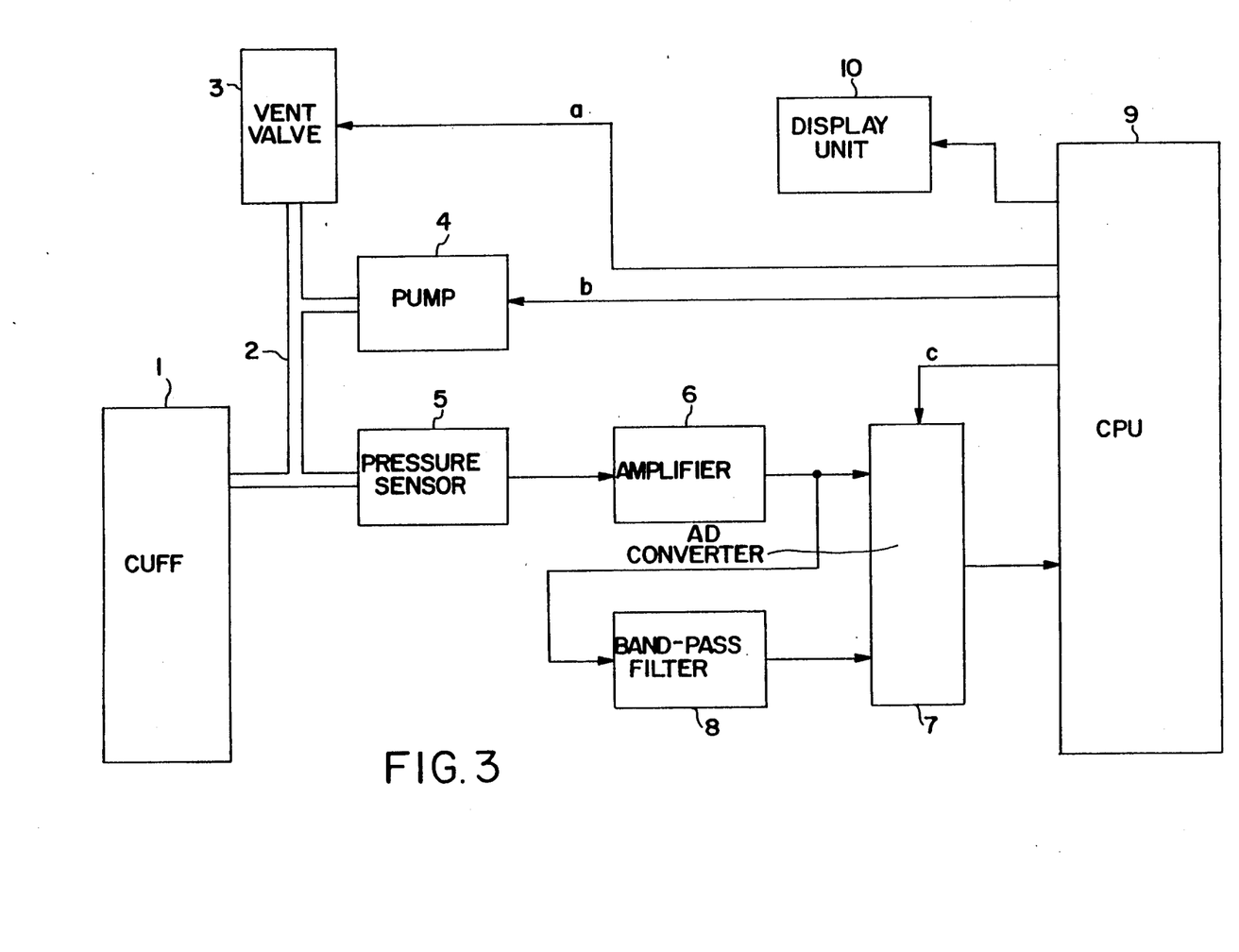
FIG. 3 is a block diagram of a first embodiment of the electronic blood pressure meter according to the present invention.

FIG. 3 is a block diagram of the hardware structure of a first embodiment of the electronic blood pressure meter according to the present invention. A cuff 1 is connected to a vent valve 3 which is capable of both rapid and gradual venting, a pressurization pump 4, and a pressure sensor 5, via a conduit 2. The pressurization pump 4 is turned on and off by command from a CPU 9, and the vent valve 3 is also activated for rapid venting or gradual venting, as required, by a command signal from the CPU 9. The pressure sensor 5 converts the pressure in the cuff transmitted thereto through the conduit 2 into an electric signal which is in turn amplified by an amplifier 6 and converted into a digital signal by an AD converter 7 so as to be received by the CPU 9.

A pulse wave component contained in the cuff pressure signal supplied from the amplifier 6 is extracted by a band-pass filter 8, and is again converted into a digital signal so as to be received by the CPU 9. The CPU 9 executes various processes required for computing blood pressure values, and the results are displaced on a display unit 10.

The hardware structure of this electronic blood pressure meter is so far not different from those of conventional electronic blood pressure meters. The pressure sensor 5 may consist of a semiconductor pressure sensor, a combination of a bellows type sensor and an oscillator, or any other by itself known pressure sensor element. The band-pass filter 8 may consist of a digital filter which is embodied by the CPU 9 according to an appropriate program. Primary features of the present invention will be found in the algorithm for computing blood pressure values which is executed in the CPU 9.

Now the operation of the blood pressure meter is described in the following with reference to the flow charts given in FIGS. 4 and 5.

Figure 4:
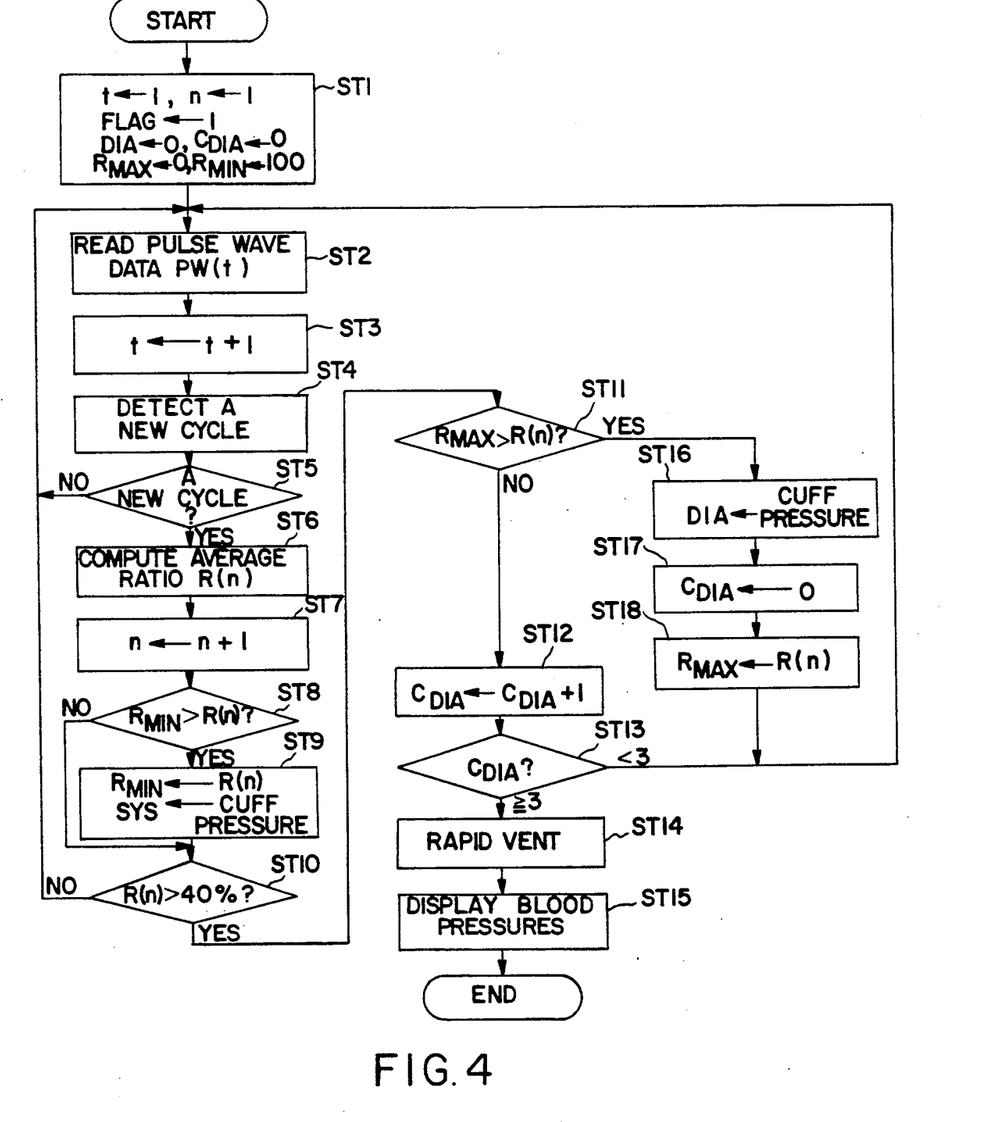
FIG. 4 is a main flow chart for the control of the first embodiment of the electronic blood pressure meter.
Figure 5:
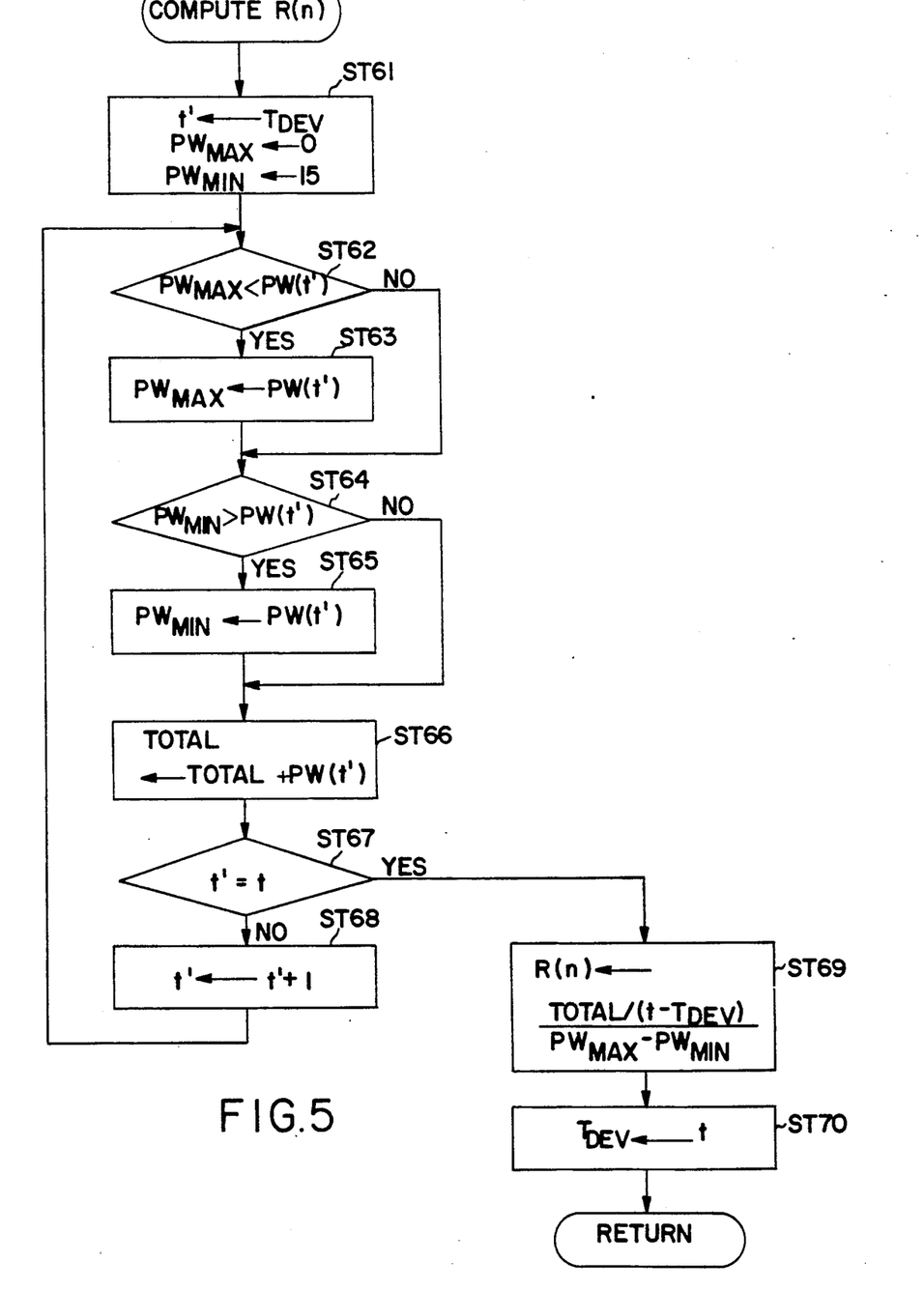
FIG. 5 is a flow chart showing in detail the process of computing average pulse wave ratios included in the main flow chart of the first embodiment.

When the start switch is turned on, the steps shown in FIG. 4 are carried out in a sequential manner. First of all, various variables for computing blood pressure values are initialized in step 1 (ST1). The important variables used in this algorithm include t or the count of pulse wave data PW(t), n or the count of pulses (or the count of the number of the computed average pulse wave ratio values), FLAG or a flag from dividing the pulse wave for each pulse, DIA or a diastolic blood pressure (which is initialized as it also has the function of a flag), $C_{DIA}$ or the count for identifying the location of a maximum point of the average pulse wave ratio (or the number of pulse counts from the maximum point to the current point of the average pulse wave ratio), and $R_{MAX}$ and $R_{MIN}$ or maximum and minimum values of the average pulse wave ratio.

Figure 6:
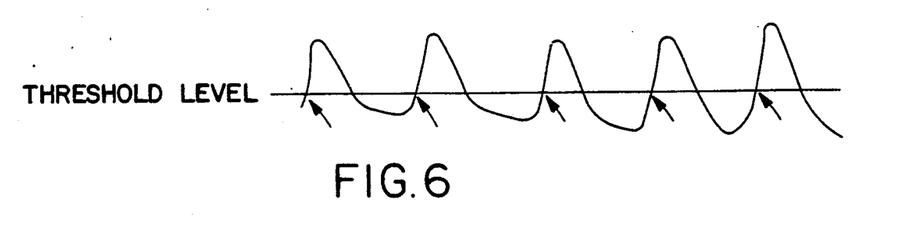
FIG. 6 is a wave form diagram illustrating the division of each cycle of the pulse wave.

Following the initialization process, the pulse wave data PW(t) is read out via the AD converter 7 (ST2), and the variable t is incremented (ST3) so that the beginning of a new cycle of the pulse wave may be detected (ST4). The beginning of a new cycle of the pulse wave is detected as such by crossing of a threshold level forming a part of the pulse wave data by the pulse wave level as illustrated in FIG. 6. It is then determined whether the beginning of a new cycle has been detected or not (ST5), and the steps in ST2 through ST5 are repeated or reading of the pulse wave data PW(t) is continued unit the beginning of a new cycle has been detected. When the beginning of a new cycle of the pulse wave is detected or the determination result of ST5 is yes, an average pulse wave ratio value R(n) is computed in ST6 as described in more detail hereinafter with reference to FIG. 5.

When an average pulse wave ratio R(n) is derived in ST6, the variable n is incremented in ST7, and variables $R_{MIN}$ and R(n) are compared in ST8. If $R_{MIN}$ is larger than R(n), the value of R(n) is placed in $R_{MIN}$ to update it, and the value of the cuff inner pressure at this moment is stored in the variable SYS (ST9). If the variable $R_{MIN}$ is found to be smaller than R(n), ST9 is skipped, and the program flow advances to ST10 where the cuff pressure when the average pulse wave ratio took the minimum value is stored as the systolic blood pressure in the variable SYS.

It is determined in ST10 whether the value of R(n) is larger than 40% of the amplitude of the pulse wave or not. If the value of R(n) is less than this 40% level, the program flow returns to ST2. Otherwise, the program flow advances to ST11 where it is determined whether the variable $R_{MAX}$ is smaller than R(n) or not. The comparison of the value of R(n) with the 40% level was performed in ST10 so that an abnormal diastolic blood pressure value may not be computed by carrying out the process of determining a diastolic blood pressure before the cuff pressure has not come sufficiently close to the true diastolic blood pressure level. In other words, as long as the cuff pressure has not been depressurized close to the diastolic blood pressure level, the process flow repeats the process of determining a systolic blood pressure by jumping from ST10 to ST2 since the average pulse wave ratio R(n) remains smaller than the 40% level. However, when the cuff is sufficiently depressurized and the average pulse wave ratio value R(n) exceeds the 40% level, the determination result of ST10 changes to yes, and the steps from ST11 onward are carried out.

If the variable $R_{MAX}$ is found to be smaller than the average pulse wave ratio R(n) in ST11, the cuff pressure value is stored in the variable DIA in ST16 and the count $C_{DIA}$ is set to zero (ST17). Further, the current average pulse wave ratio value R(n) is stored in $R_{MAX}$ (ST18), and the program flow returns to ST2. Thereafter, the steps in ST2 through ST11, ST16 through ST18 are repeated. In other words, the variable DIA is updated by the cuff pressure until the average pulse wave ratio R(n) reaches a maximum value.

If the average pulse wave ratio R(n) is found to be smaller than variable $R_{MAX}$ in ST11, the program flow advances to ST12 where the counter $C_{DIA}$ is incremented. The count $C_{DIA}$ corresponds to the number of pulses after the average pulse wave ratio R(n) passed its maximum level or after the variable $R_{MAX}$ ceased to be updated. This count $C_{DIA}$ is evaluated in ST13, and the program flow returns to ST2 as long as this count is less than 3. When this count $C_{DIA}$ is equal to or larger than 3 or the determination result of ST13 is yes, as it means that three pulses were counted without encountering any larger value of the average pulse wave ratio and the last obtained maximum value should be determined as the diastolic blood pressure, the process of blood pressure determination is terminated by rapidly venting the cuff 1 in ST14, and the obtained blood pressure values are displayed on the display unit 10 (ST15).

Now the process of computing the average pulse wave values R(n) in ST6 is described in the following in more detail by referring to the flow chart of FIG. 5.

First of all, the variables are initialized in ST61. Here, t' is a time count for the process of computing the average pulse wave ratio described hereinafter, and $T_{DEV}$ is the time count t at the beginning of the previous cycle of the pulse wave. Therefore, by substituting the value of the variable $T_{DEV}$ into the variable t', a series of steps for computing the average pulse wave ratio can be started from the beginning of the previous cycle of the pulse. $PW_{MAX}$ and $PW_{MIN}$ are variables representing the maximum and minimum values of the average pulse wave data.

The value of the pulse wave data PW(t') is compared with the variable $PW_{MAX}$ in ST62. If $PW_{MAX}$ is smaller than PW(t'), PW(t') is substituted into $PW_{MAX}$ to update it (ST63). In other words, $PW_{MAX}$ stores the maximum value of PW(t') which has been encountered so far. Therefore, when PW(t') is found to be smaller than $PW_{MAX}$, ST63 is skipped. PW(t') is then compared with $PW_{MIN}$ in ST64. If $PW_{MIN}$ is larger than PW(t'), PW(t') is substituted into $PW_{MIN}$ to update it (ST65). In other words, $PW_{MIN}$ stores the minimum value of PW(t') which has been encountered so far. In ST66, PW(t') is added up to the variable TOTAL.

The count t' is compared with the variable t representing the current time in ST67, and if t'=t or a series of steps have been carried out to the current dividing point, the program flow advances to ST69. On the other hand if t' is not equal to t, the program flow returns to ST62 to repeat the aforementioned steps after t' is incremented (ST68). In ST69, the average pulse wave ratio is computed from the variable TOTAL, the count t, the count $T_{DEV}$, $PW_{MAX}$, and $PW_{MIN}$ at the previous dividing point, according to the following formula:

$$\text{average pulse wave ratio} = \frac{TOTAL/(t - T_{DEV})}{PW_{MAX} - PW_{MIN}}$$

The time t at the current dividing point is then stored in the variable $T_{DEV}$ to prepare for the next process of computing the average pulse wave ratio, and the process is completed by the program flow returning to the main flow.

In the above description, the average pulse wave ratio was obtained during gradual depressurization of the cuff, and the diastolic blood pressure and the systolic blood pressure were obtained by detecting the critical points of the changes in the average pulse wave ratio. But, it is also possible to obtain the average pulse wave ratio during gradual pressurization of the cuff, and obtain a diastolic blood pressure and a systolic blood pressure by detecting the critical points of the changes in the average pulse wave ratio.

Thus, according to the present invention, as compared with conventional oscillometric electronic blood pressure meters, even more accurate and quick measurement is possible without being affected by individual differences.

Figure 9:
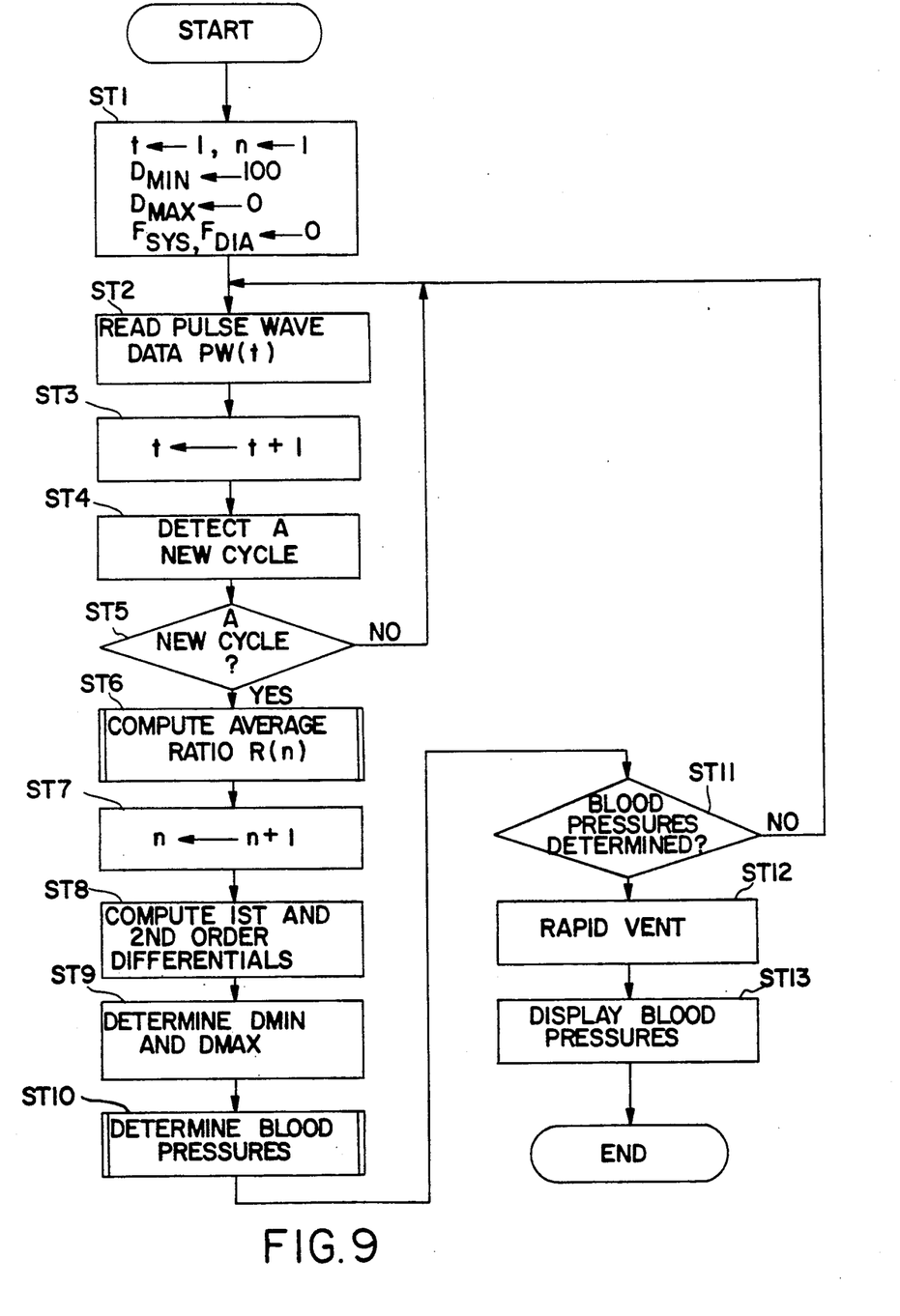
FIG. 9 is a main flow chart of the control for a second embodiment of the electronic blood pressure meter according to the present invention.
Figure 10:
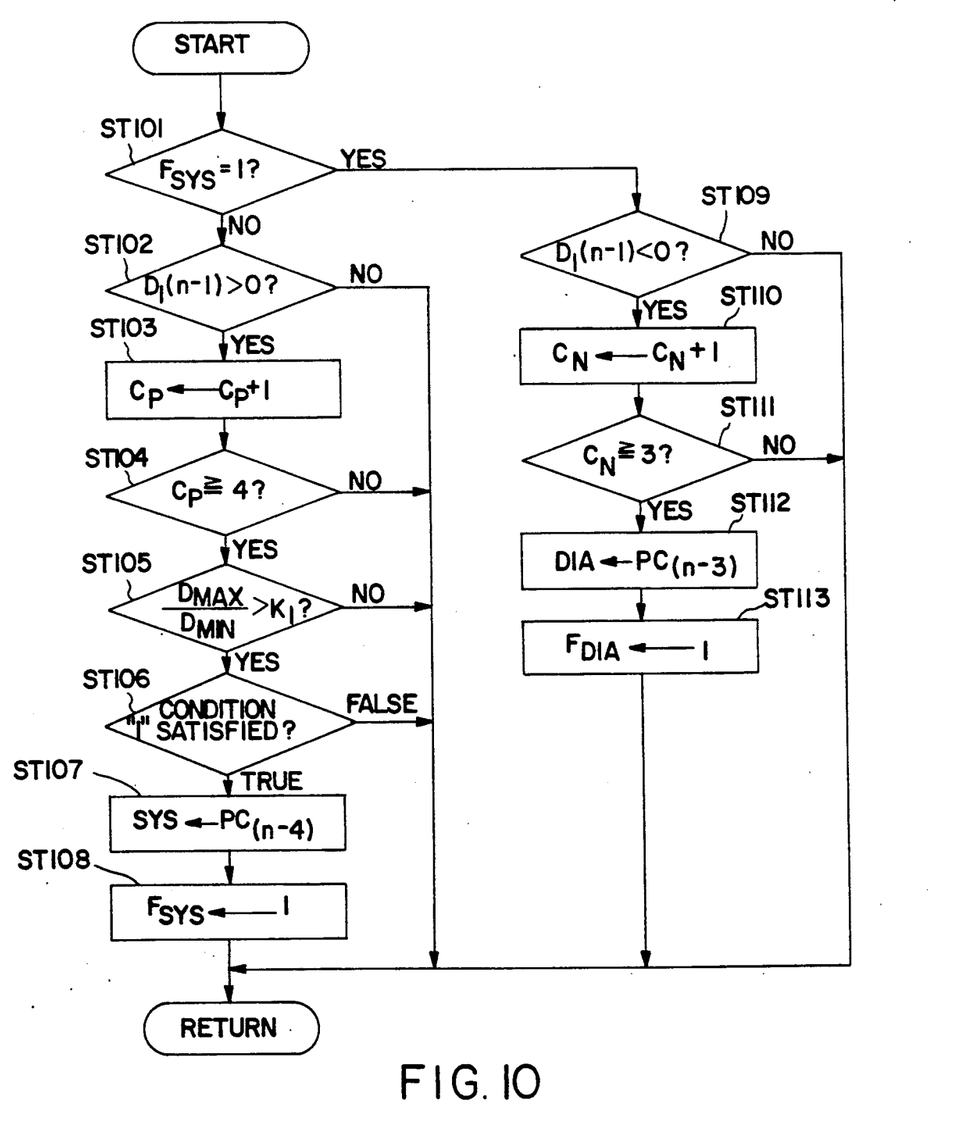
FIG. 10 is a flow chart showing in detail the process of determining blood pressures included in the main flow chart of the second embodiment.

FIGS. 9 and 10 are flow charts of the control process of a second embodiment of the present invention. The second embodiment is based on the fact that the average pulse wave ratio increases monotonically and linearly as the cuff inner pressure declines from a systolic pressure to a diastolic pressure. This embodiment may have a same hardware structure as the first embodiment.

When the start switch is turned on, the steps shown in FIG. 9 are carried out in a sequential manner. First of all, various variables for computing blood pressure values are initialized in step 1 (ST1). The important variables used in this algorithm include t or the count of pulse wave data PW(t), n or the count of pulses (or the count of the number of the computed average pulse wave ratio values), $D_{MIN}$ and $D_{MAX}$ or the minimum and maximum values of first order differentials of the average pulse wave ratio, and $F_{SYS}$ and $F_{DIA}$ are flags to indicate that a systolic pressure and a diastolic pressures have been obtained, respectively.

Following the initialization process, the pulse wave data PW(t) is read out via the AD converter 7 (ST2), and the variable t is incremented (ST3) so that the beginning of a new cycle of the pulse wave may be detected (ST4). The beginning of a new cycle of the pulse wave is detected as such by crossing of a threshold level forming a part of the pulse wave data by the pulse wave level as illustrated in FIG. 6. It is then determined whether the beginning of a new cycle has been detected or not (ST5), and the steps in ST2 through ST5 are repeated or reading of the pulse wave data PW(t) is continued until the beginning of a new cycle has been detected. When the beginning of a new cycle of the pulse wave is detected or the determination result of ST5 is yes, an average pulse wave ratio value R(n) is computed in ST6 in the same way as described previously with reference to FIG. 5.

When an average pulse wave value R(n) is derived in ST6, the variable n is incremented in ST7, and a first order differential $D_1(n)$ and a second order differential $D_2(n)$ are computed in ST8 according to the following formulae:

$$D_1(n) = R(n) - R(n-1)$$

$$D_2(n) = D_1(n) - D_1(n-1).$$

Then, the minimum value $D_{MIN}$ and the maximum value $D_{MAX}$ of the first order differentials of the average pulse wave ratio R(n) are updated by the computed value of the first order differential $D_1(n)$ of the average pulse wave ratio. Thus, the minimum value $D_{MIN}$ and the maximum value of the first order differential $D_{MAX}$ store the minimum and maximum slope values of the average pulse wave ratio R(n) which have been encountered from the start of measurement. According to these values, the process of determining blood pressure values is conducted in ST10 as described in more detail hereinafter.

If a diastolic blood pressure and a systolic blood pressure are found to be both determined in ST11, the program flow advances to ST12. Otherwise, the program flow returns to ST2 and repeats the steps in ST2 through ST11. Completion of blood pressure measurement is determined by the fact that the systolic blood pressure completion flag $F_{SYS}$ and the diastolic blood pressure completion flag $F_{DIA}$ are both "1". When the system flow advances to ST12 following completion of blood pressure measurement, the vent valve 3 rapidly vents and releases the cuff inner pressure. Then, the measured blood pressure values are displayed on the display unit 10 (ST13), and the entire process of blood pressure measurement is completed.

Now the process of determining blood pressure values in ST10 is described in more detain in the following with reference to the flow chart of FIG. 10.

The systolic blood pressure determination flag $F_{SYS}$ is examined in ST101 to find out if $F_{SYS}=1$ or not, or if a systolic blood pressure value has been determined or not. If $F_{SYS}=0$ or no systolic blood pressure value has been determined yet, the program flow advances to ST102 and the subsequent steps of determining a systolic blood pressure value.

In ST102 through ST106, it is determined whether the average pulse wave ratio R(n) has entered an interval of linear increase. It is determined whether the first order differential $D_1(n)$ is positive or not. $D_1(n) > 0$ means the average pulse wave ratio R(n) is increasing and, therefore, may well have entered an interval of linear increase as can be understood from FIG. 11(b). In this case, the count Cp is incremented in ST103. Conversely, if $D_1(n)$ is found to be equal to or less than zero in ST102, the program flow simply returns to the main flow as there is no possibility of the average pulse wave ratio having entered an interval of linear increase.

The count Cp represents the number of pulses detected after the average pulse wave ratio R(n) started increasing. This count Cp is evaluated in ST104. If the count is equal to or larger than 4, it is estimated that the average pulse wave ratio R(n) is increasing, and the program flow advances to ST105. If the count Cp is found to be less than 4, no trend of increase in the average pulse wave ratio R(n) can be estimated, and the program flow simply returns to the main flow.

Figure 11A:
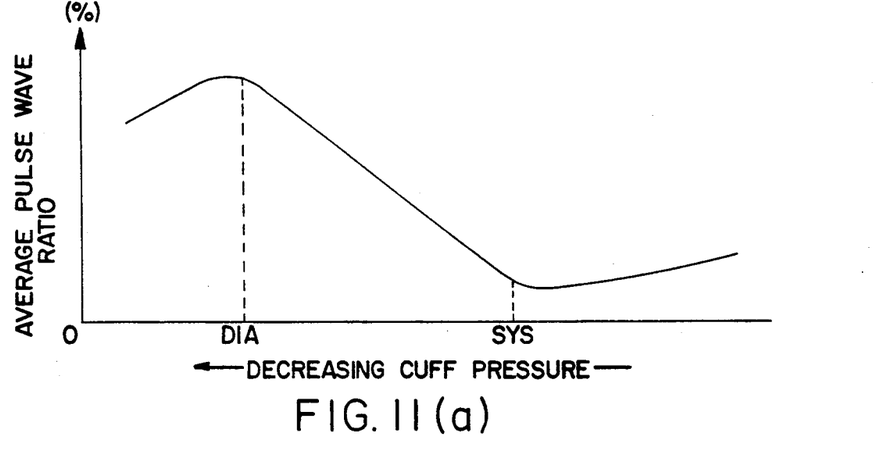
FIGS. 11(a) through 11(c) are graphs showing the changes in the average pulse wave ratios, the first order differentials thereof and the second order differentials thereof with the decline of the cuff inner pressure.
Figure 11B:
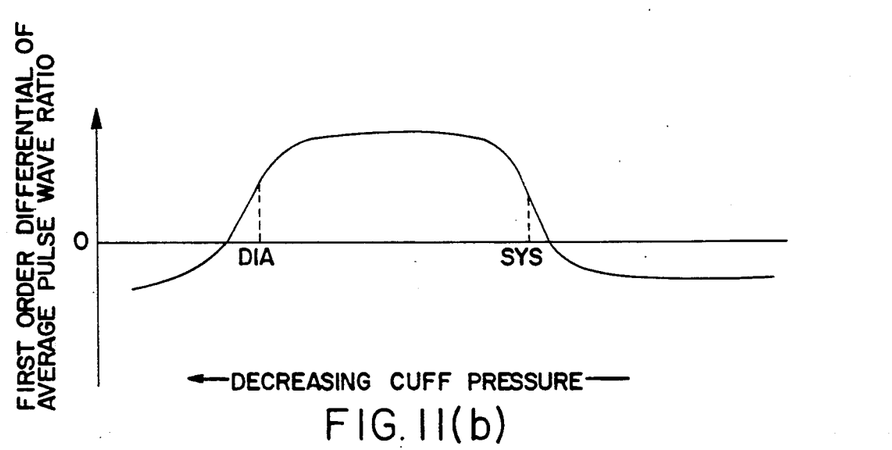
Figure 11C:
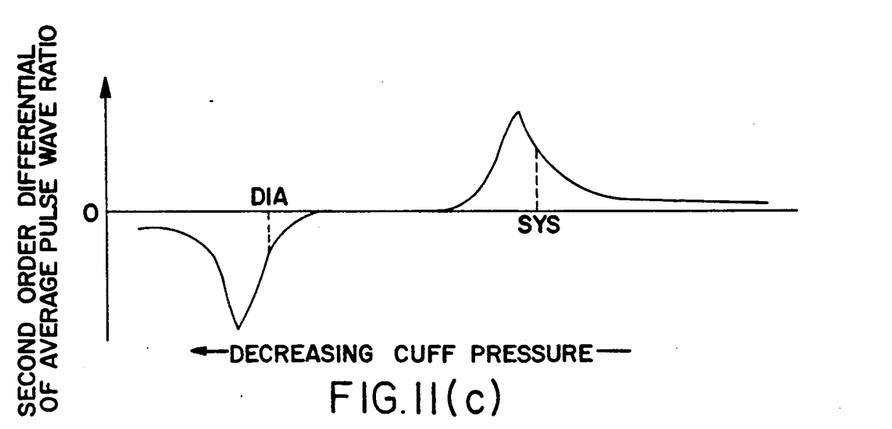

In ST105, the ratio $D_{MAX}/D_{MIN}$ of a maximum value $D_{MAX}$ of the first order differential $D_1(n)$ to a minimum value $D_{MIN}$ of the first order differential $D_1(n)$ is compared with a constant K1. This determination process is intended to detect a linear increase in the average pulse wave ratio R(n) and makes use of the fact that the average pulse wave ratio starts increasing at a higher increase rate than the preceding decrease rate as soon as it enters an interval of linear increase as shown in FIG. 11(a). In other words, even when the average pulse wave ratio R(n) is estimated to have entered an interval of linear increase in ST104, it should be considered as premature unless the maximum increase rate $D_{MAX}$ after the average pulse wave ratio has been estimated to have entered the interval of linear increase is larger than the minimum decrease rate $D_{MIN}$ encountered before entering the interval of linear increase by a certain factor K1, for instance 4. This prevents the control system to be affected by spurious noises.

When $D_{MAX}/D_{MIN}$ is found to be equal to or larger than K1 in ST105, it is assumed that the average pulse wave ratio R(n) has indeed entered an interval of linear increase, and the program flow advances to ST106 where it is determined whether the sum of the second order differential values $D_2(n)$ after entering the interval of linear increase is equal to or less than a certain constant K2 or not or whether the following condition holds or not:

$$D_2(n)+D_2(n-1)<=K2$$

Figure 8:
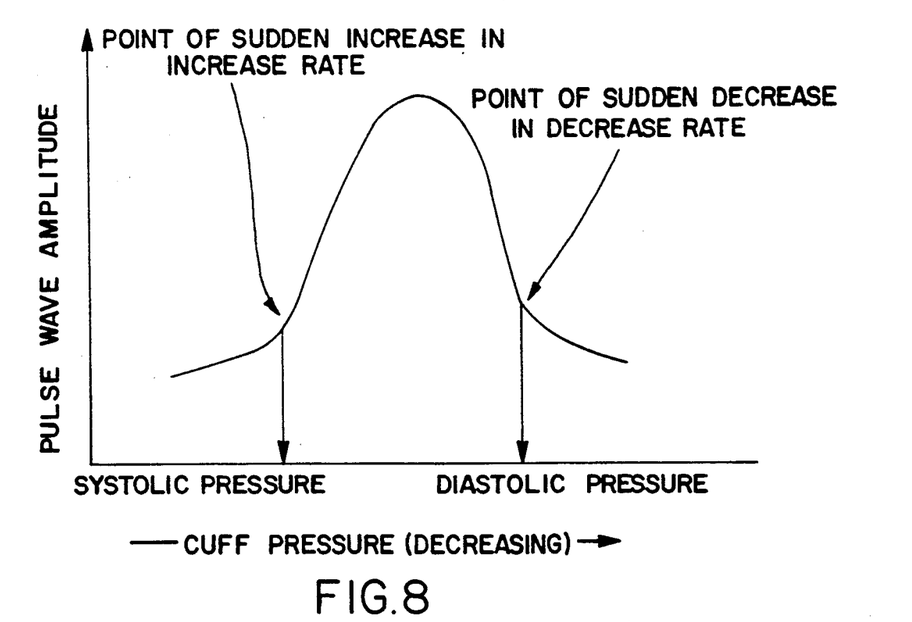

This is also intended to increase the reliability of the process of detecting an interval of linear increase and makes use of the fact that the second order differential $D_2(n)$ in the interval of linear increase is almost zero as shown in FIG. 8(c). If the sum of the second differential values after entering the interval of linear increase becomes larger than the constant K2, the estimation of the onset of the interval of linear increase is canceled, and the system flow returns to the main flow. If the estimation is upheld, the program flow advances to ST107.

In ST107, the cuff inner pressure value Pc(n−4) of four pulses back or at the time when the average pulse wave ratio R(n) entered the interval of linear increase is stored in the variable SYS, and the program flow returns to the main flow after setting the systolic blood pressure determination flag $F_{SYS}$ to "1".

If the systolic blood pressure determination flag $F_{SYS}$ is found to be "1" in ST101, the process of determining a diastolic blood pressure value is carried out in ST109 through ST113. First of all, it is determined whether the first order differential value $D_1(n-1)$ is positive or negative in ST109. If the first order differential $D_1(n-1)$ is negative, the average pulse wave ratio R(n) is decreasing and it may be estimated that the interval of linear increase has ended. If the first order differential $D_1(n-1)$ is equal to zero or positive, the program flow returns to the main flow as it is estimated that the interval of linear increase is still maintained. If $D_1(n-1)$ is negative, the count $C_N$ is incremented in ST110. The count $C_N$ represent the number of pulses which have occurred after the average pulse wave ratio ceased to increase. If this count $C_N$ is found to be 3 or larger in ST111, the program flow advances to ST112 as it is estimated that the interval of linear increase has ended. If the count is less than 3, it is still premature to conclude that the interval of linear increase has indeed ended, and the program flow again returns to the main flow.

In ST112, the cuff inner pressure value Pc(n−3) of three pulses back or at the time when the average pulse wave ratio R(n) came out of the interval of linear increase is stored in the variable DIA, and the program flow returns to the main flow after setting the diastolic blood pressure determination flag $F_{DIA}$ to "1".

Figure 12:
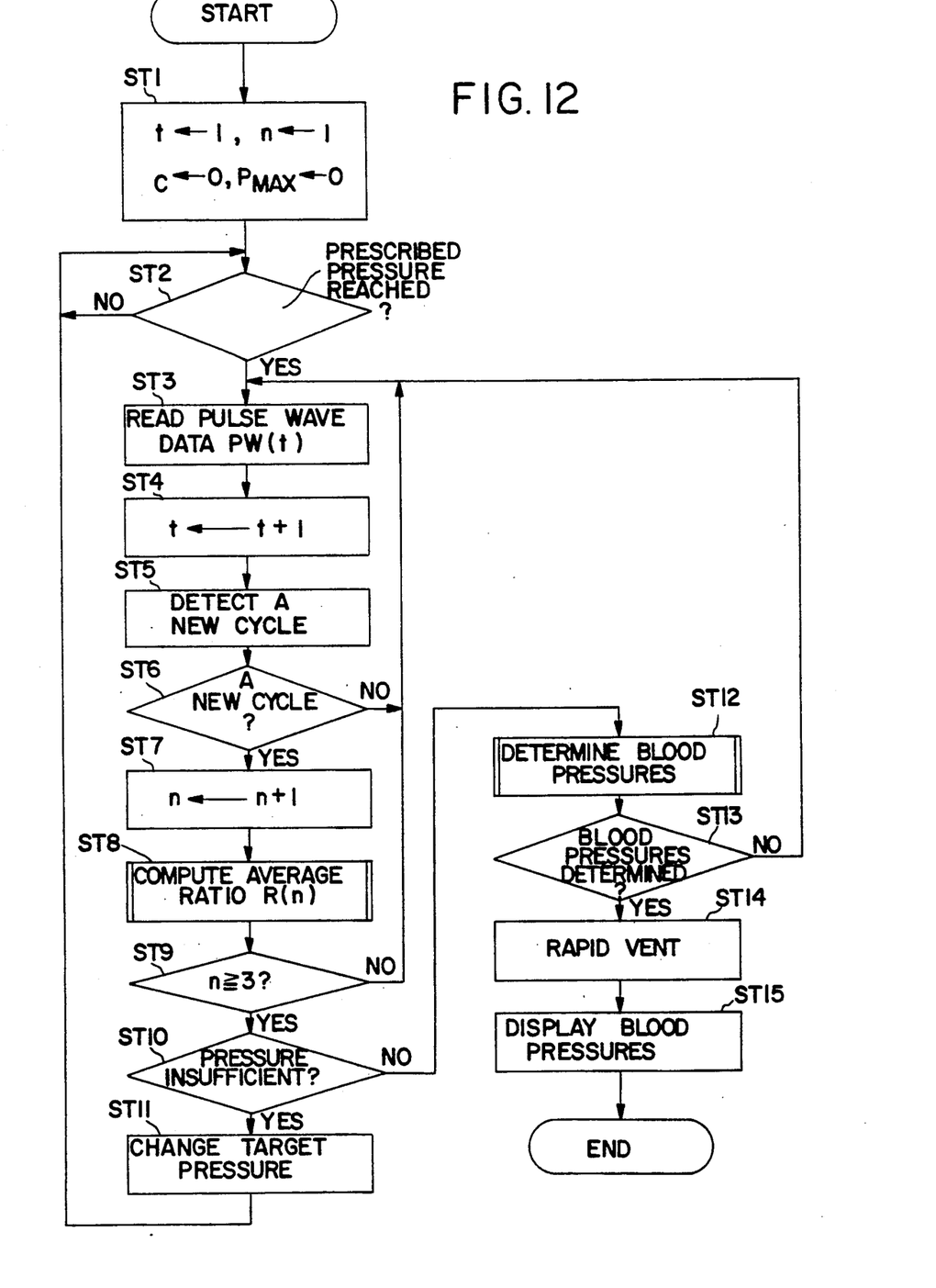
FIG. 12 is a main flow chart of the control for a third embodiment of the blood pressure meter according to the present invention.
Figure 13:
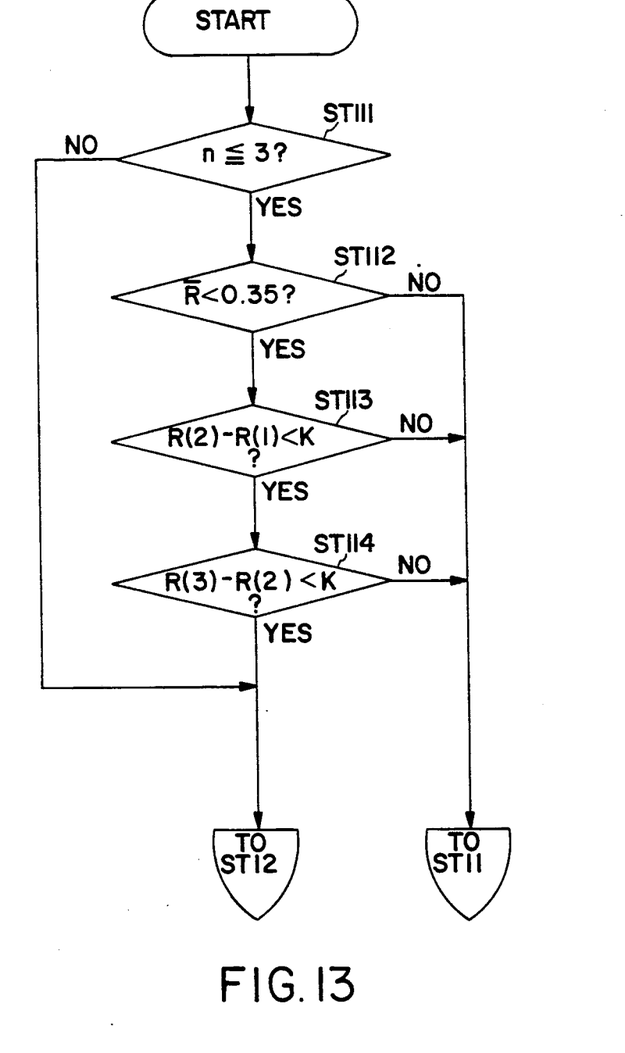
FIG. 13 is a flow chart of the control action which is activated in case of insufficient cuff pressurization.
Figure 14:
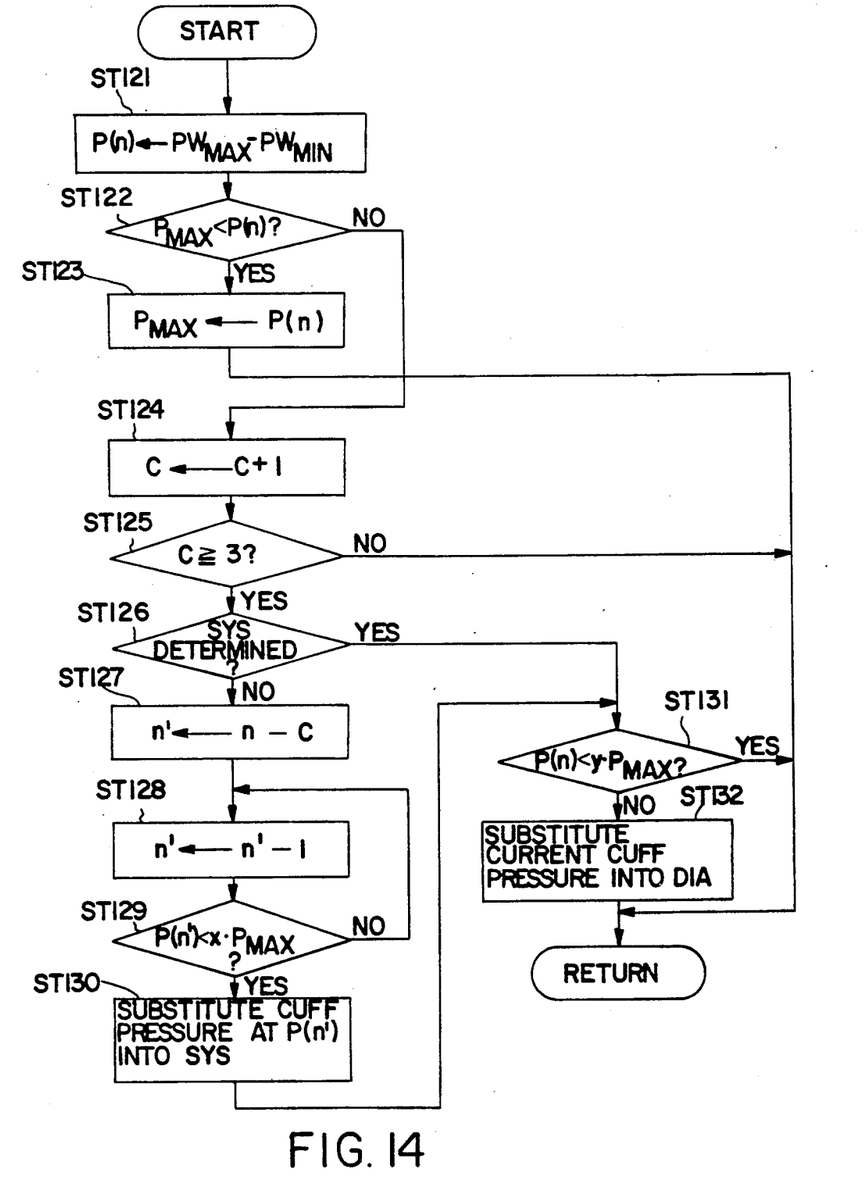
FIG. 14 is a flow chart showing in detail the process of determining blood pressures included in the main flow chart of a third embodiment.

FIGS. 12 through 14 are flow charts of the control process of a third embodiment of the present invention. This embodiment may also have a same hardware structure as the first embodiment.

When the start switch is turned on, the steps shown in FIG. 12 are carried out in a sequential manner. First of all, various variables for computing blood pressure values are initialized in step 1 (ST1). The important variables used in this algorithm include t or the count of pulse wave data PW(t), n or the count of pulses (which is also the count of the computed average pulse wave ratio values), C or a count used for determining blood pressure values, and a variable $P_{MAX}$ for storing the maximum value of the pulse wave amplitude.

Following the initialization process, the pressurization pump 4 is activated and pressurization of the cuff 1 is started in ST2. When it is detected that the cuff inner pressure has reached a prescribed level, the pressurization pump 4 is deactivated. This prescribed level may be selected by the user. Then, while the cuff 1 is gradually depressurized through gradual venting of the vent valve 3, the pulse wave data PW(t) is read out via the AD converter 7 (ST3), and the variable t is incremented (ST4) so that the beginning of a new cycle of the pulse wave may be detected (ST5). The beginning of a new cycle of the pulse wave is detected as such by crossing of a threshold level forming a part of the pulse wave data by the pulse wave level as illustrated in FIG. 6. It is then determined whether the beginning of a new cycle has been detected or not (ST6), and the steps in ST3 through ST6 are repeated or reading of the pulse wave data PW(t) is continued until the beginning of a new cycle has been detected. When the beginning of a new cycle of the pulse wave is detected or the determination result of ST6 is yes, the variable n is incremented (ST7) and an average pulse wave ratio value R(n) is computed (ST8) as described previously with reference to FIG. 5.

When an average pulse wave value R(n) is derived in ST8, it is determined whether n is equal to or larger than 3 or not in ST9. If n is less than 3, the program flow returns to ST3 to repeat the steps of ST3 through ST9 as R(1) through R(3) are required in the subsequent process of detecting insufficient pressurization. Insufficiency of pressurization is determined in ST10 as described hereinafter.

If pressurization is found to be insufficient in ST10, the target value of pressurization is changed to a new value (ST11), and repressurization is carried out in ST2 followed by the steps of ST3 through ST10. If pressurization is found to be sufficient in ST10, the program flow advances to ST12 where the process of determining blood pressure values is carried out as described hereinafter.

It is then determined in ST13 whether a systolic blood pressure and a diastolic blood pressure have already been both determined or not in ST13. If they have already been determined, the program flow advances to ST14. Otherwise, the program flow returns to ST3 to repeat the steps of ST3 through ST13. The cuff is rapidly depressurized through rapid venting of the vent valve 3 in ST14, and the obtained blood pressure values are displayed on the display unit 10 ST15 before concluding the entire process of blood pressure measurement.

Now the process which is to be carried out in case of insufficient pressurization of the cuff in ST10 is described in the following with reference to FIG. 13.

First of all, it is determined in ST111 whether the count n is equal to or less that 3 or not. If n>3, the program flow simply jumps to ST12 because it means that sufficiency of pressurization has already been evaluated and there is no need to carry out the process of ST112 onward. If n=3 (the cases for n<3 have already been eliminated in ST9), an average of three values of the average pulse wave ratio is computed according to the following formula:

$$R_{AVE} = [R(1) + R(2) + R(3)]/3$$

and it is compared with a threshold value, for instance 0.35 in ST112. If $R_{AVE}$ is equal to or larger than 0.35, the program flow advances to ST11 or it is concluded that the pressurization of the cuff was insufficient. If $R_{AVE}$ is less than 0.35, the program flow advances to ST113 where the difference between R(2) and R(1) is compared with a constant K. If R(2)−R(1) is equal to or larger than K, R(n) is neither stabilized nor decreasing, and the program flow jumps to ST11 as it should be determined that the pressurization was insufficient. However, if R(2)−R(1) is larger than K, the program flow advances to ST114 as the sufficiency of the cuff pressurization is uncertain. In ST114, sufficiency of pressurization is determined according to the average pulse wave ratio values R(3) and R(2) in a similar way as ST113. If R(3)−R(2) is found to be less than K, it is then concluded that the pressurization was surely sufficient, and the program flow advances to the step of blood pressure determination step of ST12. If R(3)−R(2) is found to be equal to or larger than K in ST104, the program flow jumps ST11 as a case of insufficient cuff pressurization.

Now the process of blood pressure determination is described in the following with reference to the flow chart of FIG. 14.

In ST121, the difference between the maximum value $PW_{MAX}$ and the minimum value $PW_{MIN}$ in the same cycle of the pulse wave obtained by the process of computing the average pulse wave ratio is computed as a pulse wave amplitude P(n). This pulse wave amplitude P(n) is compared with a variable $P_{MAX}$ in ST122. If $P_{MAX} < P(n)$, P(n) is substituted into $P_{MAX}$ in ST123 to thereby update $P_{MAX}$, and the program flow returns to the main flow. On the other hand, if $P_{MAX}$ is equal to or larger than P(n), the program flow advances to the subsequent steps without updating $P_{MAX}$. In other words, as long as the $P_{MAX}$ is updated by P(n), the amplitude of the pulse wave is increasing and the program flow returns to the main flow as it can be estimated that the maximum point has not been reached yet. Otherwise, it is estimated that the maximum point has been reached, and the process of ST124 is carried out.

In ST124, the count C is incremented. This count indicates the number of pulses which have occurred after the $P_{MAX}$ ceased to be updated. In ST125, if C is found to be equal to or larger than 3, as there is a good chance that the maximum point has been reached, the program flow advances to ST126. Otherwise, drawing of a conclusion is deferred, and the program flow returns to the main flow.

When it is finally concluded that the maximum point has been reached, it is determined whether a systolic blood pressure SYS has been determined or not. If a systolic blood pressure value SYS has not been determined, the program flow advances to the subsequent step of determining a systolic blood pressure. If a systolic blood pressure has already been determined, the program flow jumps to the steps ST131 and ST132 for determining a diastolic blood pressure value.

In ST127, n-c is substituted into the count n′ where n is the current pulse count, c is the pulse count after the occurrence of the maximum point, and n′ is therefore the pulse count upon occurrence of the maximum point. Thereafter, n′ is decremented in ST128, and the pulse wave amplitude P(n′) corresponding to this count n′ is compared with $xP_{MAX}$ in ST129. x is a constant not larger than 1 which is defined as a threshold level in the pulse wave amplitude to determining a systolic blood pressure value. Therefore, when it is found that $P(n') < xP_{MAX}$ (ST129) as n′ is sequentially decremented in ST128, the cuff pressure at this instance is determined as a systolic blood pressure (ST130).

When the program flow advances from ST126 to ST131, the current pulse wave amplitude P(n) is compared with $yP_{MAX}$ (ST131). When P(n) is found to be less than $yP_{MAX}$ (ST131), the system flow simply returns to the main flow. When P(n) is found to be equal to or larger than $yP_{MAX}$ (ST131), the cuff pressure at this instance is determined as a diastolic blood pressure (ST132) before the system flow returns to the main flow.

As can be readily understood by a person skilled in the art, the process of determining the sufficiency of cuff pressurization described in conjunction with the third embodiment can also be applied to the first and the second embodiments of the present invention.

Although the present invention has been shown and described with reference to the preferred embodiments thereof, it should not be considered as limited thereby. Various possible modifications and alterations could be conceived of by one skilled in the art to any particular embodiment, without departing from the scope of the invention.

What we claim is:
1. An electronic blood pressure meter, comprising:
   a cuff for applying a pressure to a living body whose blood pressure is to be measured;
   pressurization means for initially pressurizing said cuff and then gradually depressurizing it;
   pressure detecting means for detecting pressure in said cuff as a pulse wave as said cuff is gradually depressurized;
   pulse wave extracting means for extracting pulse wave data from said a pressure signal obtained by said pressure detecting means;
   blood pressure computing means for computing a systolic blood pressure value and a diastolic blood pressure value according to said pulse wave data obtained by said pulse wave extracting means; and
   average pulse wave ratio computing means for computing an average pulse wave ratio as a ratio of a difference between an average pulse wave level and a minimum pulse wave level to a difference between a maximum pulse wave level and the minimum pulse wave level;

said average pulse wave ratio being used by said blood pressure computing means for evaluating a relationship between said cuff pressure and said pulse wave data display means for displaying the output of said blood pressure computing means.

2. An electronic blood pressure meter according to claim 1, wherein said blood pressure computing means detects a maximum value and a minimum value of said average pulse wave ratio as said cuff pressure is gradually decreased, and determines the cuff pressures at those critical points as a systolic blood pressure value and a diastolic blood pressure value, respectively.

3. An electronic blood pressure meter according to claim 1, wherein said blood pressure computing means detects a start and an end of an interval of a relatively sharp and monotonical increase in said average pulse wave ratio as said cuff pressure is gradually decreased, and determines the cuff pressures at those critical points as a systolic blood pressure value and a diastolic blood pressure value, respectively.

4. An electronic blood pressure meter according to claim 3, wherein said blood pressure computing means detects said interval of a relatively sharp and monotonical increase by evaluating the magnitudes of second order differentials of said average pulse wave ratio.

5. An electronic blood pressure meter according to claim 1, wherein said blood pressure computing means detects insufficiency of initial pressurization of said cuff when said average pulse wave ratio at an early stage of pressurization of said cuff is larger than a certain threshold level.

6. An electronic blood pressure meter according to claim 1, wherein said blood pressure computing means detects insufficiency of initial pressurization of said cuff when an average value of a certain number of average pulse wave ratio values obtained at an early stage of pressurization of said cuff is larger than a certain threshold level.

7. An electronic blood pressure meter according to claim 1, wherein said blood pressure computing means detects insufficiency of initial pressurization of said cuff when an average value of a certain number of average pulse wave ratio values obtained at an early stage of pressurization of said cuff is larger than a certain threshold level and a change rate of said average pulse wave ratio is larger than another threshold level.

* * * * *